(12) United States Patent
Gregory et al.

(10) Patent No.: US 7,270,020 B2
(45) Date of Patent: Sep. 18, 2007

(54) INSTRUMENT ASSEMBLIES AND ANALYSIS METHODS

(75) Inventors: Mark Gregory, Lafayette, IN (US); Dennis Barket, West Lafayette, IN (US); John W Grossenbacher, West Lafayette, IN (US); Anthony Cochran, West Lafayette, IN (US)

(73) Assignee: Griffin Analytical Technologies, LLC, West Lafayette, IN (US)

( * ) Notice: Subject to any disclaimer, the term of this patent is extended or adjusted under 35 U.S.C. 154(b) by 89 days.

(21) Appl. No.: 11/152,395

(22) Filed: Jun. 13, 2005

(65) Prior Publication Data

US 2006/0010994 A1  Jan. 19, 2006

Related U.S. Application Data

(60) Provisional application No. 60/579,816, filed on Jun. 14, 2004.

(51) Int. Cl.
*G01N 30/20* (2006.01)
*F16K 11/072* (2006.01)

(52) U.S. Cl. ............... 73/864.85; 73/19.02; 73/23.22; 73/864.81; 73/864.86; 137/625.46; 137/625.47

(58) Field of Classification Search ..............................
73/864.81–864.86, 19.02, 23.22, 23.35, 73/61.52
See application file for complete search history.

(56) References Cited

U.S. PATENT DOCUMENTS 2,082,691 A * 6/1937 Farrelly ...................... 141/370
3,223,123 A * 12/1965 Young ................... 137/625.46

(Continued)

OTHER PUBLICATIONS

Vas, György and Vékey, Károly, "Solid-phase microextraction: a powerful sample preparation tool prior to mass specrometric analysis", *J. Mass Spectrom.* 2004; 39: 233-254.

Meurer, Eduardo C., et al., "Fiber Introduction Mass Spectrometry: Fully Direct Coupling of Solid-Phase Microextraction with Mass Spectrometry", *Anal. Chem.* 2002, 74, 5688-5692.

"Detection of Explosives and Chemical Warfare Agents Simulants by Coupling Fiber and Single-Sided Membrane Introduction Mass Spectrometry (SS-MIMS-FIMS)", Corre-Rodriguez, Ismael, et al., 52nd ASMS Conference, 2004.

"Fiber Introduction Mass Spectrometry", Meurer, Eduardo C., et al., Proceedings of the 50th ASMS Conference on Mass Spectrometry and Allied Topics, Orlando, Florida, Jun. 2-6, 2002.

*Primary Examiner*—Hezron Williams
*Assistant Examiner*—David A. Rogers
(74) *Attorney, Agent, or Firm*—Wells St. John P.S.

(57) ABSTRACT

The disclosure relates to instrument assemblies that can include a sample introduction port coupled to a chamber configured to receive the sample from the sample introduction port and provide analysis of the sample with a valve between the sample introduction port and the chamber. The instrument assemblies can include a septum housing assembly coupled to an analysis chamber interface with the interface including a valve and a cam rotatably mounted to the septum housing assembly and/or coupled to the valve. Analysis methods are also provided that can include introducing a sample to an instrument through both a sample introduction port and a valve coupled to the sample introduction port, and, after introducing the sample, closing the valve to seal the sample introduction port from a remainder of the instrument, with the remainder of the instrument being configured to analyze the sample after the introducing through the sample introduction port.

24 Claims, 7 Drawing Sheets

U.S. PATENT DOCUMENTS

| | | | |
|---|---|---|---|
| 3,757,981 A * | 9/1973 | Harris et al. | 215/247 |
| 3,864,978 A * | 2/1975 | Stephens | 73/863.84 |
| 3,948,104 A * | 4/1976 | Stephens | 73/863.84 |
| 4,084,440 A * | 4/1978 | Carpenter et al. | 73/863.11 |
| 4,393,726 A * | 7/1983 | Tamm et al. | 73/864.84 |
| 4,687,031 A * | 8/1987 | Goudy, Jr. et al. | 141/9 |
| 5,859,362 A | 1/1999 | Neudorfl et al. | |
| 6,042,787 A | 3/2000 | Pawliszyn | |
| 6,267,143 B1 * | 7/2001 | Schick | 137/625.11 |
| 6,354,135 B1 | 3/2002 | McGee et al. | |
| 6,390,127 B2 * | 5/2002 | Schick | 137/625.11 |
| 6,397,658 B1 | 6/2002 | Villettaz et al. | |
| 6,405,608 B1 | 6/2002 | Lindgren et al. | |
| 6,708,550 B2 | 3/2004 | McGee et al. | |
| 6,910,503 B2 * | 6/2005 | Schick et al. | 137/625.47 |

* cited by examiner

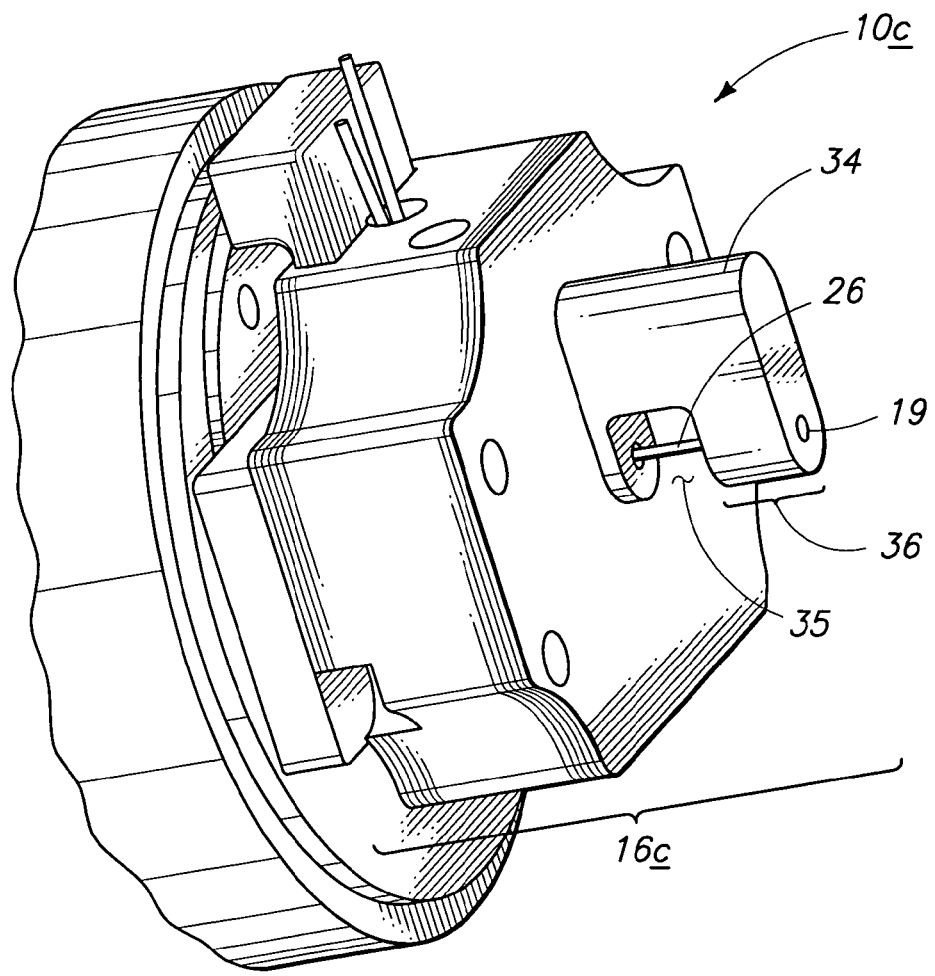

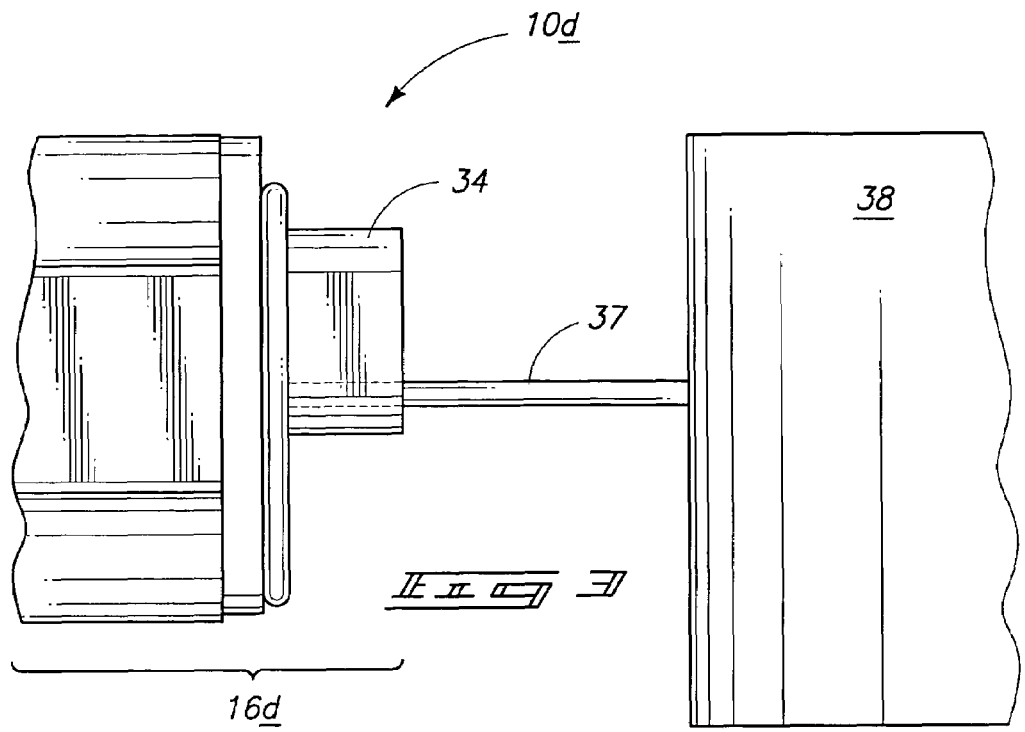
_FIG. 3_
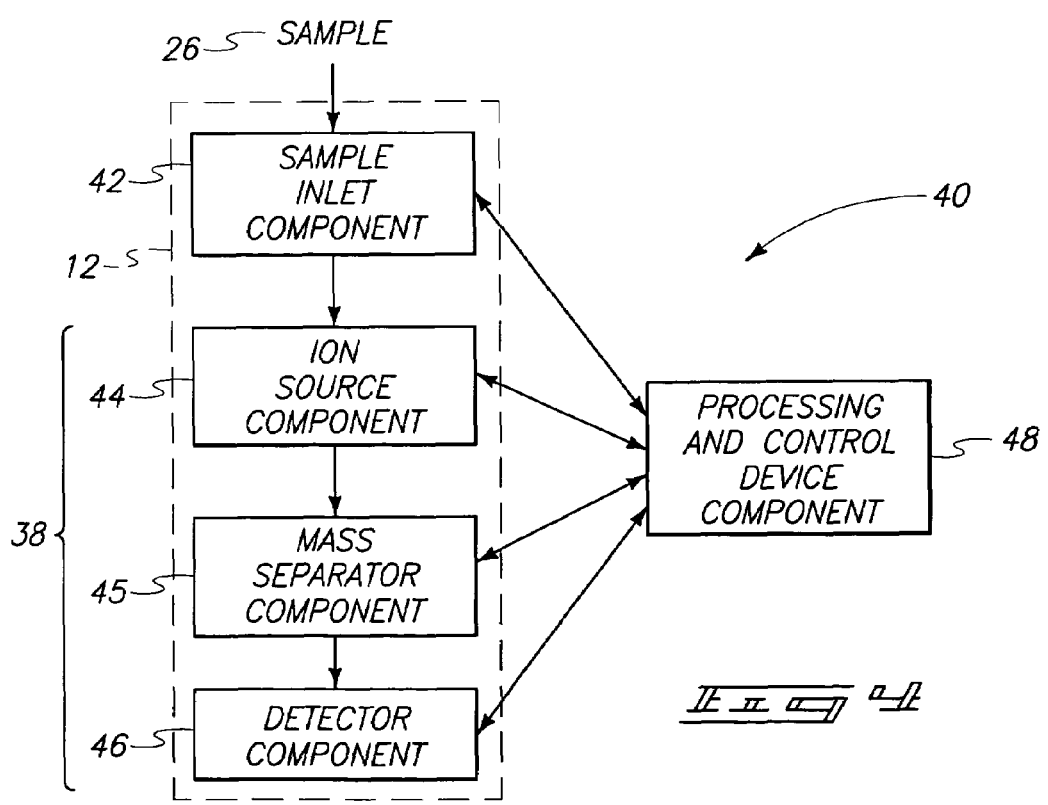
_FIG. 4_

INSTRUMENT ASSEMBLIES AND ANALYSIS METHODS

CLAIM FOR PRIORITY

This application claims priority under 35 USC § 119 to U.S. Provisional Patent Application Ser. No. 60/579,816 filed Jun. 14, 2004, entitled Sample Introduction Assemblies and Methods, the entirety of which is incorporated by reference herein.

GOVERNMENT RIGHTS STATEMENT

This invention was made with Government support under SBIR Phase I Contract M67854-04-C-3002 awarded by the United States Marine Corps. The Government has certain rights in the invention.

TECHNICAL FIELD

This disclosure relates to instrument assemblies and analysis methods generally and more particularly solid phase microextraction sampling device and mass spectrometry assemblies and methods.

BACKGROUND

Analytical instrumentation typically includes some form of sample introduction assembly or apparatus. These assemblies aid in the introduction of the sample to the instrument and can significantly impact the quality of data acquired through analysis. For example, analytical instruments such as mass spectrometers can include a mass analysis component that can require the practical absence of contaminants while maintaining a sufficient vacuum to enable the acquisition of reliable data. The introduction of sample into these components can likewise introduce contaminants and disrupt vacuum which can cause the acquisition of unreliable data and/or require instruments to be shut down until they can be decontaminated and/or pumped down to a sufficient vacuum. Samples can be introduced for analysis without providing contaminants and/or disrupting an analytical instrument's ability to acquire reliable data according to embodiments of the sample introduction assemblies and methods described.

SUMMARY

The disclosure relates to instrument assemblies that can include a sample introduction port coupled to a chamber configured to receive the sample from the sample introduction port and provide analysis of the sample. The assemblies can also include a valve between the sample introduction port and the chamber. The instrument assemblies can include a septum housing assembly coupled to an analysis chamber interface. The interface can include a valve and a cam can be rotatably mounted to the septum housing assembly and/or coupled to the valve.

The disclosure also relates to analysis methods that can include introducing a sample to an instrument through both a sample introduction port and a valve coupled to the sample introduction port. The method may continue with, after introducing the sample, closing the valve to seal the sample introduction port from a remainder of the instrument, with the remainder of the instrument being configured to analyze the sample after the introducing through the sample introduction port.

BRIEF DESCRIPTION OF THE DRAWINGS

Preferred embodiments of the invention are described below with reference to the following accompanying drawings.

FIG. 2g is an isometric view of an instrument assembly of FIGS. 2a-2c according an embodiment.

FIG. 3 is a plan view of an instrument assembly according to an embodiment.

FIG. 4 is an illustrative view of an instrument assembly according to an embodiment.

DETAILED DESCRIPTION

At least some of the embodiments provide sample analysis methods and assemblies. Exemplary configurations of these assemblies and methods are described with reference to FIGS. 1-5.

Figure 1:
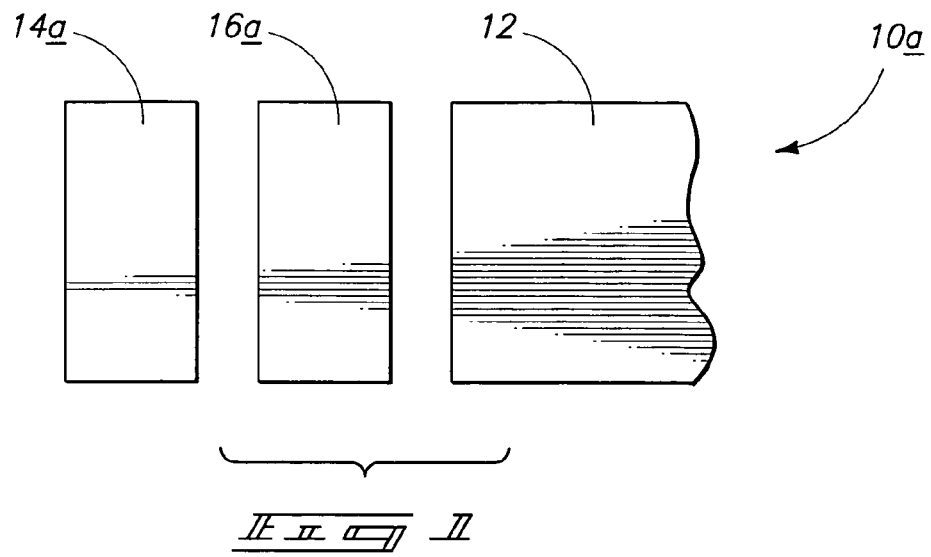
FIG. 1 is an illustrative representation of an instrument assembly according to an embodiment.

Referring to FIG. 1, an instrument assembly 10a is shown that includes an analysis chamber 12 and a sample introduction port assembly 14a, having an analysis chamber interface 16a therebetween. According to exemplary embodiments, instrument assembly 10a can be an instrument configured to perform chemical analyses such as mass analysis, including mass spectrometry analysis. Exemplary assemblies 10a include sample inlet, ion source, mass separator, detector, and processing and control components. Exemplary mass spectrometry assembly configurations can house one or more of the ion source, mass separator, and detector components within an analysis chamber such as chamber 12. Typical mass spectrometry analysis chambers are maintained under high vacuum while restricting the flow of contaminants into the analysis chamber to as few as practically possible.

Analysis chamber 12 can be coupled to interface 16a and/or sample introduction port assembly 14a. Analysis chamber 12 can be configured to receive sample from sample introduction port assembly 14a via interface 16a and, upon receipt, initiate analysis of the sample. Such sample can be in liquid, solid, and/or vapor form and can be introduced into a volume of chamber 12. Analysis of the sample within analysis chamber 12 can include heating the sample to convert at least some of the sample from the solid phase to the liquid phase, from the liquid phase to the gas phase, and/or from the solid phase to the gas phase. In an exemplary embodiment, to convert the sample to another phase, regions within analysis chamber 12 may be configured to have a higher temperature than regions of interface 16a and/or port 14a, for example. In exemplary embodiments, regions of analysis chamber 12, interface 16a, and/or port 14a may be configured with different temperatures. Analysis chamber 12 can also be configured to receive the sample and ionize at least some of the sample via an ion source component, for example. To ionize at least portions of the sample, regions within analysis chamber 12 may be configured to have lower pressures than regions of interface 16a and/or port 14a, for example. In exemplary embodiments, regions of analysis chamber 12, interface 16a, and/or port 14a may be configured with different pressures.

Sample introduction port assembly 14a can include all ports configured to receive sample and provide the sample to interface 16a and/or chamber 12. Instrument assembly 10a can be configured with sample introduction port assembly 14a being coupled to interface 16a which can be coupled to analysis chamber 12. Sample introduction port assembly 14a of instrument assembly 10a can be configured to receive sample and provide the sample through interface 16a to analysis chamber 12 without providing the sample through any other components. Such configuration can include providing the sample directly from assembly 14a through interface 16a and into chamber 12.

In exemplary embodiments, sample introduction port assembly 14a can be configured to receive sample via a syringe having a needle, as such these ports can be configured to receive a syringe needle. Port assembly 14a can be configured to receive sample from a solid phase microextraction (SPME) device. Exemplary sample introduction ports can include those utilized to introduce sample to gas chromatographs, mass spectrometers, and/or gas chromatography/mass spectrometers. Sample introduction ports can be configured to receive sample from Purge and Trap assemblies, and/or headspace sampling assemblies. Introduction port assemblies can also include pin hole sample introduction ports, skimmer cones, and/or capillary inlets, for example. Introduction ports can also include valves.

Embodiments of assembly 10a include interface 16a. Interface 16a can be coupled to chamber 12 and/or port 14a. Where assembly 10a is configured as a mass spectrometry assembly, interface 16a can be coupled to chamber 12 and, in other embodiments, interface 16a can be removably operably coupled to chamber 12. According to exemplary embodiments, interface 16a can be configured to isolate the volume of chamber 12 from port 14a. Interface 16a can include a valve that may be configured in open and closed positions, for example. Exemplary embodiments of assembly 10b include those described in International Patent Application No. PCT/US04/01144, filed Jan. 16, 2004, entitled Mass Spectrometer Assemblies, Mass Spectrometry Vacuum Chamber Lid Assemblies, and Mass Spectrometer Operational Methods, the entirety of which is incorporated by reference herein. Assembly 10b may also be configured as described in U.S. Provisional Patent Application Nos. 60/580,144, filed Jun. 15, 2004 entitled Instrument Assemblies and Methods and 60/580,582, filed Jun. 16, 2004, entitled Mass Spectrometry Instruments, the entirety of which are incorporated by reference herein.

Figure 2A:
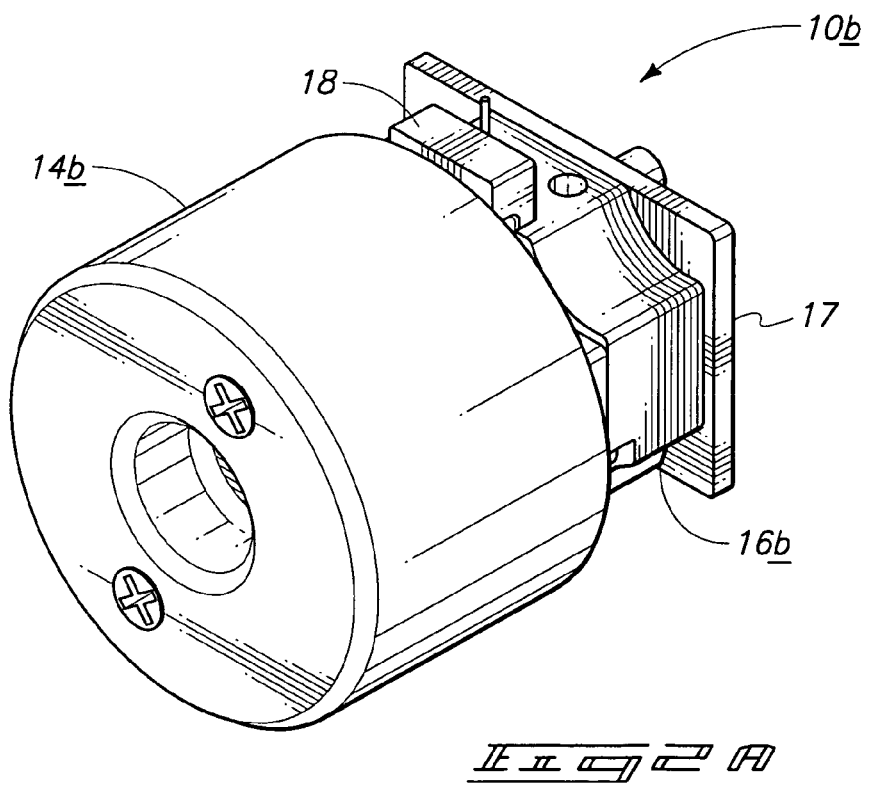
FIG. 2a is an isometric view of an instrument assembly according to an embodiment.

Referring next to FIG. 2a, an exemplary assembly 10b is shown that includes sample introduction port assembly 14b and an analysis chamber interface 16b. Interface 16b is configured to be coupled at portion 17 to an exemplary analysis chamber (e.g. FIG. 1). Interface 16b also includes a valve 18, for example.

Figure 2B:
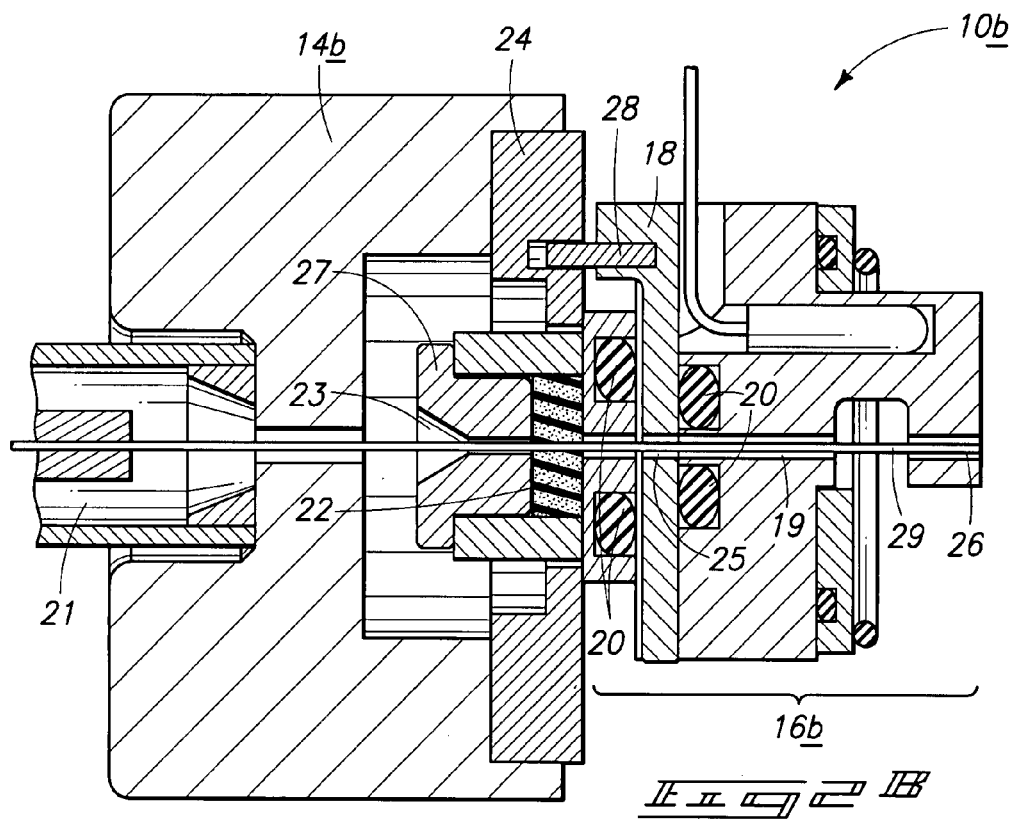
FIG. 2b is a plan view of the instrument assembly of FIG. 2a according to an embodiment.
Figure 2C:
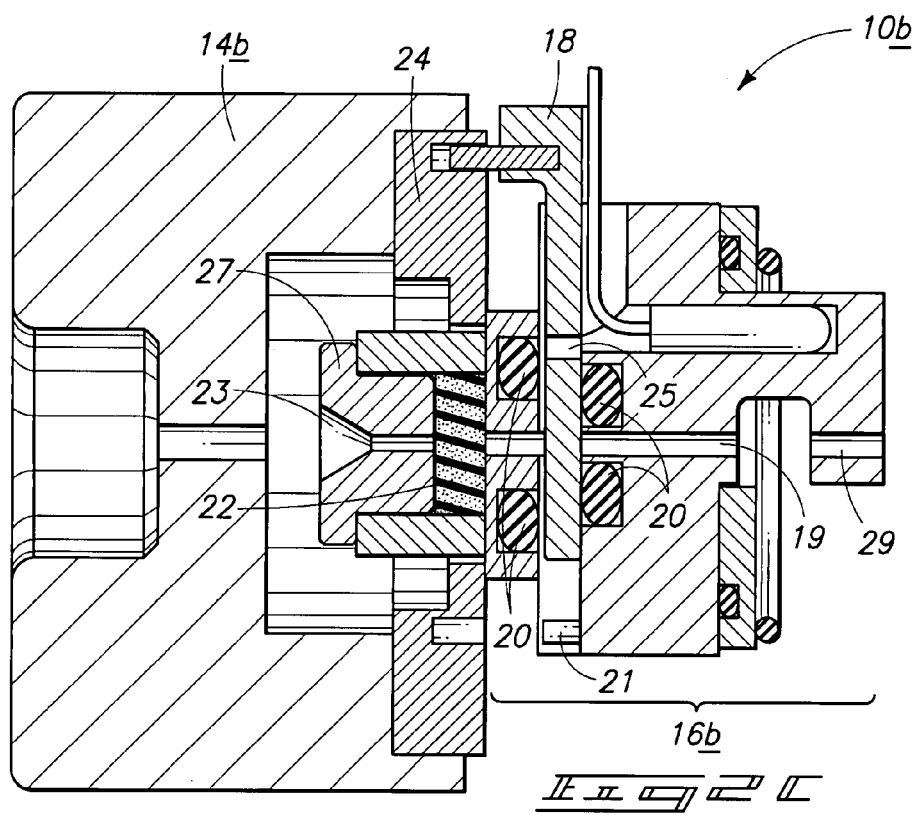
FIG. 2c is a plan view of the instrument assembly of FIGS. 2a and 2b according to an embodiment.

Referring to FIGS. 2b and 2c, cross sections of instrument assembly 10b are shown configured in two positions respectively, opened and closed, for example. With reference to FIG. 2b, assembly 10b is shown with valve 18 in the open position receiving sample via a sampling device assembly 21. As exemplarily depicted in FIGS. 2b and 2c, introduction port 14b can be configured to mate with complementary portion of sampling device assembly 21. The complementary portion of port 14b can be affixed to cam 24. In the exemplarily depicted embodiment, analysis chamber interface 16b includes an opening 19 configured to receive sample via a tube or needle 26 of sampling device assembly 21, for example. For purposes of this disclosure, the sample represents any chemical composition, including both inorganic and organic substances, in solid, liquid, and/or vapor form. Specific examples of sample suitable for analysis include volatile compounds such as toluene, or other specific examples, including highly complex non-volatile protein based structures such as bradykinin. In certain aspects, sample can be a mixture containing more than one substance or, in other aspects, sample can be a substantially pure substance. Analysis of sample can be performed according to exemplary aspects described herein.

Sampling device assembly 21 can include SPME sampling devices. In exemplary embodiments the sample can include solid substrates received from SPME devices. For example, solid phase SPME is a technique that can utilize a treated fiber to collect and transport a sample to an instrument. In exemplary configurations, the fiber is part of a device that can be similar in appearance to a hypodermic needle. Typically a fiber can be 1 cm in length and approximately 0.25 mm in diameter. Exemplary embodiments provide for the introduction of sample, such as a solid phase sample via a SPME device directly into assembly 10b. The sample can be the solid substrate used during SPME sampling and be part of a device 21 that, in some embodiments, has similar appearance to a hypodermic needle. The sample can be extended into assembly 10b through port 14b and into interface 16b via a plunger (not shown) of assembly 21. The plunger can be coupled to a small diameter tube 26 that may contain sample 29. The plunger can be used to position sample 29, a fiber for example, either within or external to the tube 26. In exemplary embodiments, the fiber can be extended from tube 26 for sample collection then withdrawn into tube 26 for transport and insertion into an analytical instrument assembly 10b and extended yet again within opening 19 for sample analysis.

Insertion of sample 29 into instrument assembly 10b can include insertion of tube 26 into introduction port assembly 14b. Assembly 10b can be configured to utilize a septum or a sample introduction seal 22. Some embodiments will then allow tube 26 of a SPME sampling device to pass into the analysis chamber (e.g. FIG. 1) without allowing ambient air or contaminants into the analysis chamber. Septum 22 may reseal the analysis chamber (e.g. FIG. 1) upon removal of tube 26 to prevent air and contaminants from leaking into the chamber (e.g. FIG. 1) and causing loss of vacuum. It has been recognized that tube 26 of a typical SPME holder may be cut perpendicular to the axis of tube 26 or have a blunt tip that may make a rough cut through septum 22 as it is pierced over time, thereby damaging septum 22 and increasing the likelihood of contaminant introduction or vacuum decrease in sample analysis chambers. It has also been recognized that when utilizing direct sample introduction, replacement of septum 22 requires that the typical instruments be shut down and the instrument analysis chamber be vented to the atmosphere thereby causing inconvenience to the user and/or increasing the likelihood that moisture or other contaminants will enter the instrument analysis chamber. Furthermore, regardless of whether SPME technology is being used for sample introduction, it has been recognized that septum 22 can fail unexpectedly and give rise to improper analysis data.

Other solid substrates may also be analyzed, such as hair and clothing materials, utilizing embodiments of assemblies and methods described herein. These substrates have been found to absorb compositions and/or react with compositions that may be desorbed from the substrates or removed from the substrates via pyrolysis and utilized to acquire the nature of the compositions acquired by the substrates.

Embodiments of assembly 10b include opening 19 of analysis chamber interface 16b configured to align with opening 23 of sample introduction port assembly 14b. In the exemplarily depicted embodiment of FIG. 2b, valve 18 is configured as a part of interface 16b and proximate sample introduction port assembly 14b. In the exemplarily depicted embodiment, valve 18 includes opening 25 that, as shown in FIG. 2b, is aligned with openings 23 and 19 providing fluid communication between sample introduction port assembly 14b, interface 16b, and/or an analysis chamber (e.g. FIG. 1). In exemplary embodiments, this fluid communication can facilitate insertion of sample 26. For example, as configured in FIG. 2b, valve 18 allows for the introduction of sample 26 into the analysis chamber (e.g. FIG. 1).

Embodiments of instrument assembly 10b include a sample introduction port assembly 14b, and assembly 14b can include a cam 24 which is coupled to valve 18. Cam 24 can be coupled to valve 18 via a portion 28 of valve 18, such as pin 28 and cam 24 can include a complementary portion to that of portion 28, such as an opening to receive the pin. Cam 24 can be rotatably coupled to a septum housing assembly 27 and/or removable from the housing assembly. Assembly 27 can be configured to house septum 22 and, as such, assembly 27 can include an introduction port cap that may be removably operably configured to allow access to septum 22 for purposes of inspection and/or replacement, for example. Septum housing assembly 27 can be coupled to the interface and/or the analysis chamber. As rotatably coupled to septum housing assembly 27, cam 24 can be configured to rotate about an axis, and septum housing assembly 27 may be centered along the axis. Valve 18 can be affixed proximate sample introduction port assembly 14b and analysis chamber interface 16b by seals 20. Exemplary seals can include o-rings.

Referring next to FIG. 2c, assembly 10b is shown as configured in the closed position. In the closed position, sample introduction port assembly 14b includes cam 24 rotated in a fashion that removes opening 25 from fluid communication with openings 23 and 19. In this configuration, an analysis chamber (e.g. FIG. 1) is effectively sealed allowing for the removal of, or exchange of, sample introduction seal 22. As exemplarily depicted in FIG. 2c, interface 16b includes a valve stop portion 21. Valve stop portion 21 can include a stop pin and can provide the stop position of valve 18 when valve 18 is in the open position as exemplarily depicted in FIG. 2b.

Figure 2D:
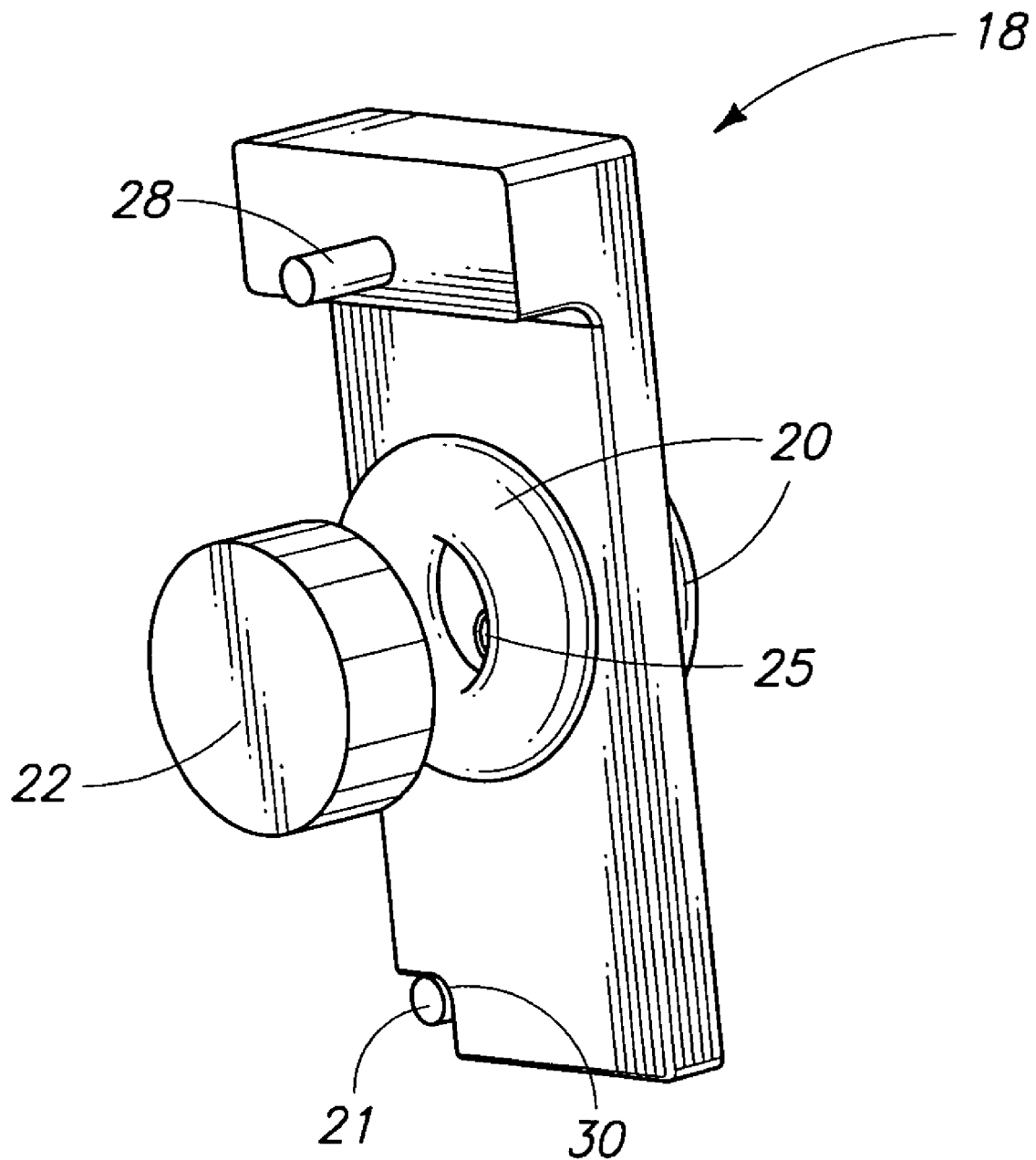
FIG. 2d is an isometric view of a component of the instrument assembly of FIGS. 2a-2c according to an embodiment.

Referring next to FIG. 2d, exemplary valve 18 is depicted that includes pin 28 configured to mate with cam 24 (FIGS. 2b and 2c) to facilitate the movement of valve 18 between open and closed positions upon rotation of cam 24, for example. Cam 24 can include an opening that may be complementary to pin 28 and, as such, facilitate mating of valve 18 and cam 24. Cam 24 can also be configured to be removable from valve 18. Valve 18 can also include recess 30 for receipt of valve stop 21, as depicted in FIG. 2c. In the exploded view of FIG. 2d, portions of interface 16b are not shown nor are portions of port assembly 14b shown. However, sample introduction seal 22 is shown aligned with opening 25 which is between seals 20. In the exemplarily depicted embodiment, seals 20 can be o-rings placed within o-ring configured grooves (e.g. FIGS. 2b and 2c) of sample introduction port assembly 14b and analysis chamber interface 16b.

Figure 2E:
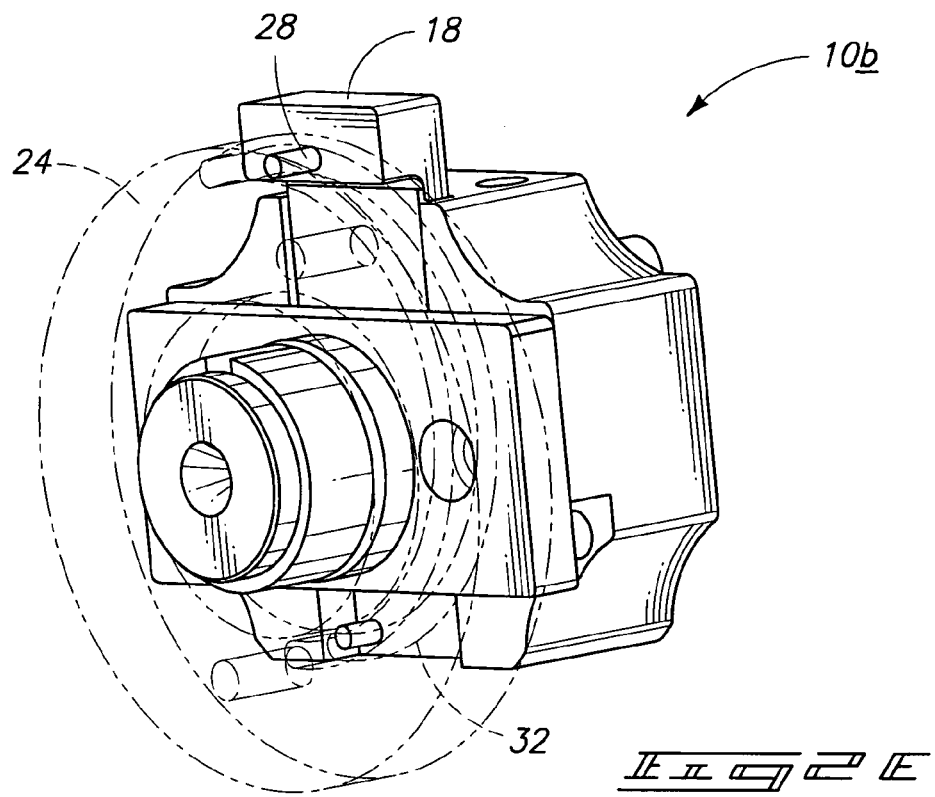
FIG. 2e is an isometric view of the instrument assembly of FIGS. 2a-2c according to an embodiment.

Referring next to FIG. 2e, instrument assembly 10b is shown in an isometric view and, as shown, includes cam 24 which includes groove 32. An end of cam 24 can comprise and/or be rotatably mounted to either or both the sample introduction port assembly and the valve, for example. In accordance with an exemplary embodiment, cam 24 can include groove 32 that takes the form of a radial arc which center is offset from an axis about which cam 24 can be configured to rotate. As depicted, groove 32 extends into a surface of the cam proximate the interface and is configured within cam 24 from a point proximate the center portion of cam 24 to a point proximate the edge portion of cam 24. Groove 32 can also extend from a point proximate the sample introduction port. In this exemplary configuration, rotation of cam 24 can transition valve 18, when coupled to cam 24 via pin 28, between the open and closed positions. As shown in the exemplary embodiment of FIG. 2e, cam 24 is rotated into a position wherein valve 18 is in the closed position.

Figure 2F:
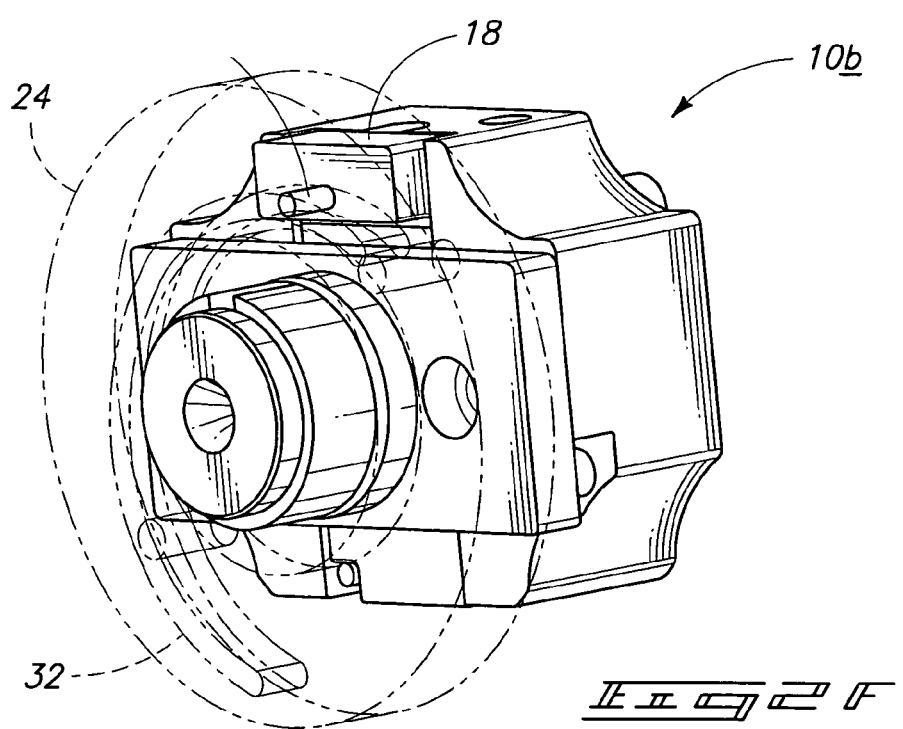
FIG. 2f is an isometric view of the instrument assembly of FIGS. 2a-2c according to an embodiment.

Referring next to FIG. 2f, assembly 10b is shown with valve 18 in the open position. Assembly 10b includes cam 24 with groove 32 coupled to pin 28 after rotation of cam 24 from the configuration of FIG. 2e, aligning valve 18 in the closed position.

Referring again to FIGS. 2a-2f, valve 18 can be used to isolate sample introduction seal 22 from analysis chamber 12. In exemplary embodiments, cam 24 can be rotated and configure valve 18 in the closed position. Upon configuration in the closed position, septum assembly 27 can be opened and introduction seal 22 can be removed, replaced, cleaned, inspected, and/or exchanged. Assembly 27 can then be closed, for example, and valve 18 returned to the open position via rotation of cam 24. Exemplary methods also include opening valve 18 to receive sample 26. Sample can be received from a syringe as described above and sample can take the form of a solid substrate, liquid, or gas sample. In exemplary embodiments, upon receipt of sample 26, valve 18 can be returned to the closed position during sample analysis. Upon closing the valve, the sample introduction port can be sealed from a remainder of the instrument assembly that is configured to receive the sample and/or analyze the sample after introduction from the sample introduction port. In exemplary embodiments, analysis methods can reduce the pressure upon introduction seal 22 extending the useful life of seal 22 and/or preventing contamination from entering the analysis chamber (e.g. FIG. 1).

Valve 18 may also be configured to transition automatically between open and closed positions. Valve 18 alone or in conjunction with cam 24 can be coupled to a motor (not shown) with the motor controlled by processing and control device component 48 (see. FIG. 4 below), for example. By way of example, processing and control device component 48 can include analytical parameters such as valve open and/or close parameters and processing and control device component 48 can be configured to associate these parameters with other analytical parameters such as analysis initiation parameters including interface heating parameters (discussed below), sample inlet component parameters, and/or ion source component parameters, for example.

Referring next to FIG. 2g, instrument assembly 10c includes a thermal focuser 34 extending from analysis chamber interface 16c. In exemplary embodiments, thermal focuser 34 can extend into an analysis chamber (e.g. FIG. 1). Thermal focuser 34 can be configured to heat sample 26 and/or tube 29 (e.g., FIG. 2b), for example. In exemplary embodiments, thermal focuser 34 can be used to facilitate the removal of analytes from sample 26. For example, where sample 26 is received as the solid substrate of a SPME sampling device, thermal focuser 34 can facilitate the evaporation and/or pyrolysis of analytes obtained during SPME sampling, as exemplarily described above. In the shown embodiment, thermal focuser 34 can include an opening 35. Exemplary embodiments of focuser 34 include configurations without opening 35, such as configurations having only opening 19 extending therethrough. The exemplary thermal focusers 34 include cartridge heaters and typical cartridge heaters can achieve up to 250° C. at sample 26. In the exemplarily depicted embodiment of FIG. 2g, thermal focuser 34 includes a larger portion 36. In exemplary embodiments, larger portion 36 can allow for the flow of heat away from the sampling port (e.g. FIGS. 2a-2f) causing the heat to be concentrated near the end of the sample thereby maximizing the heating process, in exemplary configurations. In exemplary embodiments a temperature sensor can be included that can measure the temperature of interface 16c and from that temperature, further correlate the temperature of sample 26. Typical sensors can be connected to commercially available temperature controllers that can be adjusted to a temperature set point of approximately 350° C. Power to thermal focuser 34 can be controlled and can maintain the temperature at the sensor. In exemplary embodiments, the center cartridge heater can be isolated from analysis chamber 12 to prevent contamination of the chamber. In an exemplary configuration, cam 24 may be coupled to a switch that provides power to thermal focuser 34 thereby heating the sample. The switch may be configured to engage the power when the cam is in one or both of the open or closed positions, for example.

Referring next to FIG. 3, instrument assembly 10d is shown that includes analysis chamber interface 16d. Analysis chamber interface 16d not only includes thermal focuser 34, as described above, but also includes a sample transfer tube 37. Exemplary sample transfer tube 37 can be aligned for direct insertion of sample 26 to an analyzer component 38. In exemplary embodiments, sample transfer tube 37 can provide for directing sample 26 into the volume of analyzer component 38 instead of what is typically the much larger volume of the analysis chamber (e.g. FIG. 1). In exemplary embodiments, this transfer of the sample can improve sensitivity of the measurement as well as reduce time to take a measurement.

An exemplary instrument 40, having been configured to utilize assemblies 10a-10d, is depicted in FIG. 4. Instrument 40 can be configured as described in U.S. Provisional Patent Application Nos. 60/580,144, filed Jun. 15, 2004 entitled Instrument Assemblies and Methods, and 60/580,582, filed Jun. 16, 2004, entitled Mass Spectrometry Instruments, the entirety of which are incorporated by reference herein. As configured as a mass spectrometer, instrument 40 can be configured to receive sample 26 into sample inlet component 32. For purposes of this disclosure, sample inlet component 42 can include, or be configured as, assemblies 10a-10d as described above. Analysis of sample 26 can be performed according to exemplary aspects described below.

As represented in FIG. 4, components 40 can include a sample inlet component 42 operationally connected to an ion source component 44 which can be operationally connected to a mass separator component 45 which can be operationally connected to a detector component 46. These general components can be operationally connected to a processing and control device component 48. Exemplary embodiments provide for the use of components 40 to perform mass spectrometry. Components 40 can be operationally connected as shown in FIG. 4 or operationally connected in other configurations enabling mass spectrometry operations. Further, other arrangements including more or less or alternative components are possible.

Sample inlet component 42 can be configured to introduce an amount of sample 26 into assembly 10 (FIG. 1) for analysis. Depending upon sample 26, sample inlet component 42 may be configured to prepare sample 26 for ionization. In some aspects, sample inlet component 42 may be combined with ion source component 44.

In exemplary embodiments, chamber 12 can house mass analyzer components 38. Mass analyzer components 38 can include ion source 44, mass separator 45, and detector 46 components.

Ion source component 44 can be configured, in exemplary embodiments, to receive sample 26 directly or, in other exemplary embodiments, to receive sample 26 from sample inlet component 42. Ion source component 44 can be configured to convert portions or an entirety of sample 26 into analyte ions in one example. This conversion can include the bombardment of sample 26 with electrons, ions, molecules, and/or photons. This conversion can also be performed by thermal or electrical energy.

Ion source component 44 may utilize, for example, electron ionization (EI, typically suitable for the gas phase ionization), photo ionization (PI), chemical ionization, collisionally activated disassociation and/or electrospray ionization (ESI). For example in PI, the photo energy can be varied to vary the internal energy of the sample. Also, when utilizing ESI, sample 26 can be energized under atmospheric pressure and potentials applied when transporting ions into a volume of exemplary chamber 12 can be varied to cause varying degrees of dissociation. Potentials applied when utilizing ESI can be varied to cause varying degrees of dissociation as described in International Application number PCT/US04/012849 filed Apr. 26, 2004, entitled Instrumentation, Articles of Manufacture, and Analysis Methods, the entirety of which is incorporated by reference herein. Furthermore, exemplary ion source components include those described in U.S. Provisional Patent Application No. 60/585,113 filed Jul. 2, 2004, entitled Spectrometry Instruments, Assemblies and Methods, the entirety of which is incorporated by reference herein.

The analyte ions can proceed to mass separator component 45. Mass separator component 45 can include one or more of linear quadrupoles, triple quadrupoles, quadrupole ion traps (Paul), cylindrical ion traps, linear ion traps, rectilinear ion traps, ion cyclotron resonance, quadrupole ion trap/time-of-flight mass spectrometers, or other structures. Mass separator component 45 can also include focusing lenses as well as tandem mass separator components such as tandem ion traps or ion traps and quadrupoles in tandem. In one implementation at least one of multiple tandem mass separator components can be an ion trap. Exemplary mass separators include those described in International Patent Application No. PCT/US03/38587, filed Dec. 2, 2003, entitled Processes for Designing Mass Separators and Ion Traps, Methods for Producing Mass Separators and Ion Traps, Mass Spectrometers, Ion Traps, and Methods for Analyzing Samples, the entirety of which is incorporated by reference herein. Tandem mass separator components can be placed in series or parallel. In an exemplary implementation, tandem mass separator components can receive ions from the same ion source component. In an exemplary aspect the tandem mass separator components may have the same or different geometric parameters. The tandem mass separator components may also receive analyte ions from the same or multiple ion source components.

Analytes may proceed to detector component 46. Exemplary detector components include electron multipliers, Faraday cup collectors, photographic and scintillation-type detectors. The progression of mass spectrometry analysis from sample inlet component 42 to detector component 46 can be controlled and monitored by a processing and control device component 48. Exemplary detector components also include those described in U.S. Provisional Patent Application No. 60/607,940 filed Sep. 7, 2004 entitled Mass Spectrometry Analysis Techniques and Mass Spectrometry Circuitry, the entirety of which is incorporated by reference herein.

Acquisition and generation of data can be facilitated with processing and control device component 48. Processing and control device component 48 can be a computer or mini-computer or other appropriate circuitry that is capable of controlling components 42, 44, 45, and/or 46. This control can include, for example, the specific application of voltages to ion source component 44 and mass separator component 45, as well as the introduction of sample 26 via sample inlet component 42 and may further include determining, storing and ultimately displaying mass spectra recorded from detector component 46. This control can also include the control of valve 18 (FIGS. 2a-2f) in conjunction with sample receipt. Processing and control device component 48 can contain data acquisition and searching software. In one aspect, such data acquisition and searching software can be configured to perform data acquisition and searching that includes the programmed acquisition of total analyte count. In another aspect, data acquisition and searching parameters can include methods for correlating the amount of analytes generated to predetermine programs for acquiring data. Exemplary configurations of processing and control components include those described in U.S. Provisional Patent Application No. 60/607,890 filed Sep. 7, 2004, entitled Analysis Methods and Devices, as well as International Patent Application No. PCT/US04/29029 filed Sep. 4, 2003 entitled Analysis Device Operational Programming Methods and Analysis Device Methods, the entirety of both of which are incorporated by reference herein.

Figure 5:
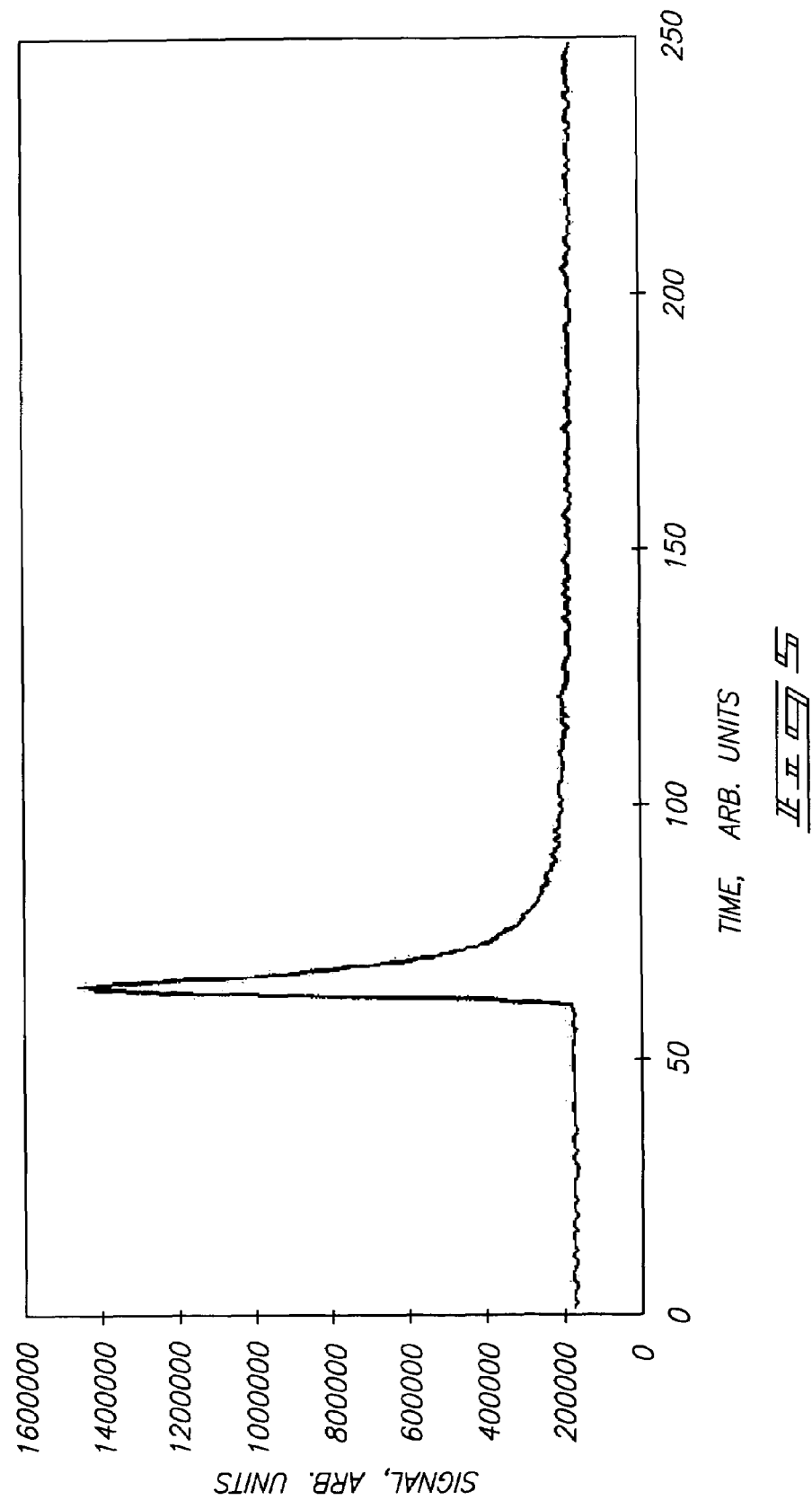
FIG. 5 is exemplary data acquired using the apparatus and methods described herein.

Referring to FIG. 5 exemplary data acquired utilizing the assemblies and methods described herein is shown. The data was acquired by direct SPME mass spectrometry analysis of Aqueous Dimethyl Methylphosphonate (DMMP).

The invention claimed is:

1. An instrument assembly comprising:
    a sample introduction port coupled to an analysis chamber, the sample introduction port being configured to receive a sample for analysis;
    a valve between the sample introduction port and the analysis chamber;
    a cam coupled to the valve, wherein the cam is rotatably mounted to the sample introduction port, the cam comprises a first end extending to a second end, the first end being both rotatably mounted to the sample introduction port and coupled to the valve, wherein the first end of the cam comprises a surface, the surface comprising an opening configured to receive a portion of the valve;
    the cam is configured to rotate about an axis, and the opening of the surface comprises a groove, the groove extending in a radial arc offset from the axis; and
    the instrument being configured to automatically rotate the cam about the axis upon occurrence of a predefined event.

2. The assembly of claim 1 wherein the valve can be configured in at least two positions, the two positions comprising a closed position and an open position, wherein, as configured in the open position, the sample introduction port is in fluid communication with the chamber.

3. The assembly of claim 1 wherein the sample introduction port, valve, and chamber are configured to receive a solid phase sample from a solid phase microextraction sampling device.

4. The assembly of claim 1 wherein the cam is configured to be removable from the valve.

5. The assembly of claim 1 wherein the introduction port is configured to receive a syringe needle.

6. The assembly of claim 5 wherein the introduction port comprises a septum, the septum being configured to be pierced by the syringe needle upon introduction of the sample.

7. The assembly of claim 1 wherein:
    the introduction port comprises at least one region having a first temperature; and
    the chamber comprises at least another region having a second temperature, the first temperature being different from the second temperature.

8. The assembly of claim 7 wherein the first temperature is less than the second temperature.

9. The assembly of claim 1 wherein the opening of the cam is configured to mate with a sampling device.

10. The assembly of claim 9 wherein the sampling device comprises a solid phase microextraction syringe.

11. The assembly of claim 1 wherein the valve is configured to receive a stop pin.

12. The assembly of claim 11 wherein the valve can be configured in at least two positions, the two positions comprising a closed position and an open position, wherein as configured in the open position, the valve contacts the stop pin.

13. The assembly of claim 1 wherein the opening comprises a groove and the portion of the valve comprises a pin, the groove and pin being configured to couple.

14. The assembly of claim 13 wherein the groove comprises a first end extending to a second end, the second end being proximate the sample introduction port, wherein the groove is configured to transition the pin from the first end to the second end of the groove upon rotation of the cam.

15. The assembly of claim 14 wherein the valve can be configured in at least two positions, the two positions comprising a closed position and an open position, wherein:
    in the closed position, the pin is proximate the first end of the groove; and
    in the open position, the pin is proximate the second end of the groove.

16. An analysis method comprising:
    introducing a sample to an instrument through both a sample introduction port and a valve coupled to the sample introduction port, wherein, the sample introduction port comprises a septum assembly having a cam rotatably mounted thereto; and
    after introducing the sample, closing the valve to seal the sample introduction port from a remainder of the instrument, the remainder of the instrument being configured to analyze the sample after the introducing through the sample introduction port, the closing comprising rotating the cam about the septum assembly.

17. The method of claim 16 further comprising, prior to introducing the sample, opening the valve to provide fluid communication between the sample introduction port and the remainder of the instrument.

18. The method of claim 17 wherein the opening the valve comprises rotating a cam, the cam being rotatably coupled to the sample introduction port.

19. The method of claim 16 wherein the introducing the sample comprises mating a portion of a sampling device with a complementary portion of the sample introduction port.

20. The method of claim 19 wherein the complementary portion is rotatably coupled to the sample introduction port.

21. The method of claim 20 wherein the closing the valve comprises rotating the complementary portion about an axis, the axis being aligned with the sample introduction port.

22. An analysis method comprising:
   introducing a sample to an instrument, the instrument comprising a sample introduction port and a remainder of the instrument, the remainder of the instrument configured to receive the sample from the sample introduction port, wherein a portion of the sample introduction port is in fluid communication with the remainder of the instrument during at least a portion of the introducing;
   after the portion of the introducing, sealing the portion of the sample introduction port from the remainder of the instrument; and
   after sealing the portion of the sample introduction port from the remainder of the instrument, heating a portion of the remainder of the instrument, the heating converting at least a portion of the sample from liquid phase to gas phase, wherein the sealing comprises rotating a portion of the sample introduction port about an axis aligned with the port, the rotating beginning the heating of the portion of the remainder of the instrument.

23. The method of claim 22 wherein the introducing the sample comprises heating the sample, the heating converting at least a portion of the sample from liquid phase to gas phase.

24. The method of claim 22, further comprising, prior to introducing the sample, configuring the instrument to receive the sample, the configuring comprising rotating a portion of the sample introduction port about an axis aligned with the port, the rotating ceasing the heating of the portion of the remainder of the instrument.

* * * * *